United States Patent [19]

Miller et al.

[11] Patent Number: 5,180,581
[45] Date of Patent: Jan. 19, 1993

[54] BIOLOGICAL INSECT CONTROL AGENTS AND METHODS OF USE

[75] Inventors: Lois K. Miller; David R. O'Reilly, both of Athens, Ga.

[73] Assignee: University of Georgia Research Foundation, Inc., Athens, Ga.

[21] Appl. No.: 373,952

[22] Filed: Jun. 29, 1989

[51] Int. Cl.$^5$ .................... A01N 63/00; C12N 15/01
[52] U.S. Cl. ........................... 424/93 A; 435/172.3; 935/59; 935/64
[58] Field of Search .................... 435/69.1, 70.21; 424/93, 405; 530/350

[56] References Cited

PUBLICATIONS

Dougherty et al. (1987) Physiol. Entomol. 12:23-30.
Truman, J. W., et al., "Physiology of Insect Rhythms III. The Temporal Organization of the Endocrine Events Underlying Pupation of the Tobacco Hornworm", *J. Exp. Biol.*, vol. 60, pp. 371-382 (1974).
Steel, C. G. H., et al., "Integration in the Insect Endocrine System", In *Comprehensive Insect Physiology and Biochemistry and Pharmacology*, G. Kerkut and L. Gilbert, eds., vol. 8, pp. 1-35 (1985).
Koolman, J., et al., "Regulation of Ecdysteroid Titer: Degration", In *Comprehensive Insect Physiology and Biochemistry and Pharmacology*, G. Kerkut and L. Gilbert, eds., vol. 7, pp. 343-361 (1985).
Entwistle, P. F., et al., "Viral Control", In *Comprehensive Insect Physiology and Biochemistry and Pharmacology*, G. Kerkut and L. Gilbert, eds., vol. 12, pp. 347-412 (1985).
Huber, J., "Use of Baculoviruses in Pest Management Programs", In *The Biology of Baculoviruses*, R. Granados and B. Federici, eds., vol. II, pp. 181-202 (1986).
Miller, L. K., et al., "Bacterial, Viral, and Fungal Insecticides", *Science*, vol. 219, pp. 715-721 (1983).
Kirschbaum, J. B., "Potential Implication of Genetic Engineering and Other Biotechnologies to Insect Control", *Annual Review of Entomology*, vol. 30, pp. 51-70 (1985).
Miller, L. K., "Expression of Foreign Genes in Insect Cells", In *Biotechnology in Invertebrate Pathology and Cell Culture*, K. Maramorosch, ed., pp. 295-303 (1987).
Keeley, L. L., et al., "Speculations on Biotechnology Applications for Insect Neuroendocrine Research", *Insect Biochemistry*, vol. 17, pp. 639-651 (1987).
Miller, D. W., "Genetically Engineered Viral Insecticides", In *Biotechnology for Crop Protection*, P. Heldin, J. Menn and R. Hollingworth, eds., pp. 405-421 (1988).

Warren, J. T., et al., "Metabolism of Ecdysteroids During the Embryogenesis of *Manduca Sexta*", *Journal of Liquid Chromatography*, vol. 9, pp. 1759-1782 (1986).
Thompson, M. J., et al., "Metabolism of 26-[14C] Hydroxyecdysone 26-Phosphate in the Tobacco Hornworm, *Manduca sexta* L., to a New Ecdysteroid Conjugate: 26-[14C] Hydroxyecdysone 22-Glucoside", *Archives of Insect Biochemistry and Physiology*, vol. 4, pp. 1-15 (1987).
Miller, L. K., et al., "Restriction Endonuclease Analysis for the Identification of Baculovirus Pesticides", *Applied and Environmental Microbiology*, vol. 35, pp. 411-421 (1978).
Lee, H. H., et al., "Isolation of Genotypic Variants of *Autographa californica* Nuclear Polyhedrosis Virus", *Journal of Virology*, vol. 27, pp. 754-767 (1978).
Miller, L. K., et al., "Physical Map of the DNA Genome of *Autographa californica* Nuclear Polyhedrosis Virus", *Journal of Virology*, vol. 29, pp. 1044-1055 (1979).
Potter, K. N., et al., "Correlating Genetic Mutations of a Baculovirus with the Physical Map of the DNA Genome", In *Animal Virus Genetics*, B. Fields, R. Jaenisch, and C. Fox, eds., pp. 71-80 (1980).
Pennock, G. D., et al., "Strong and Regulated Expression of *Escherichia coil* b-Galactosidase in Insect Cells with a Baculovirus Vector", *Molecular and Cellular Biology*, pp. 399-406 (1984).
Kunmar, S., et al., "Effects of serial passage of *Autographa californica* nuclear polyhedrosis virus in cell culture", *Virus Research*, vol. 7, pp. 335-349 (1987).

Primary Examiner—Richard A. Schwartz
Assistant Examiner—John Leguyader
Attorney, Agent, or Firm—Greenlee and Winner

[57] ABSTRACT

Insect control agents comprising a gene coding for a protein that affects the growth, development or behavior of an insect. The gene is either activated to prevent insect molting and pupation or is inactivated to reduce the feeding behavior, inhibit growth and result in the earlier death of the insect host. Methods for producing the insect control agent and methods of controlling insects by exposing them to the insect control agent are also included. An *Autographa californica* nuclear polyhedrosis virus in which the naturally occurring ecdysteroid UDP-glucosyl transferase gene was inactivated was demonstrated to have advantages over the wild-type *Autographa californica* nuclear polyhedrosis virus as in insect control agent.

5 Claims, 13 Drawing Sheets

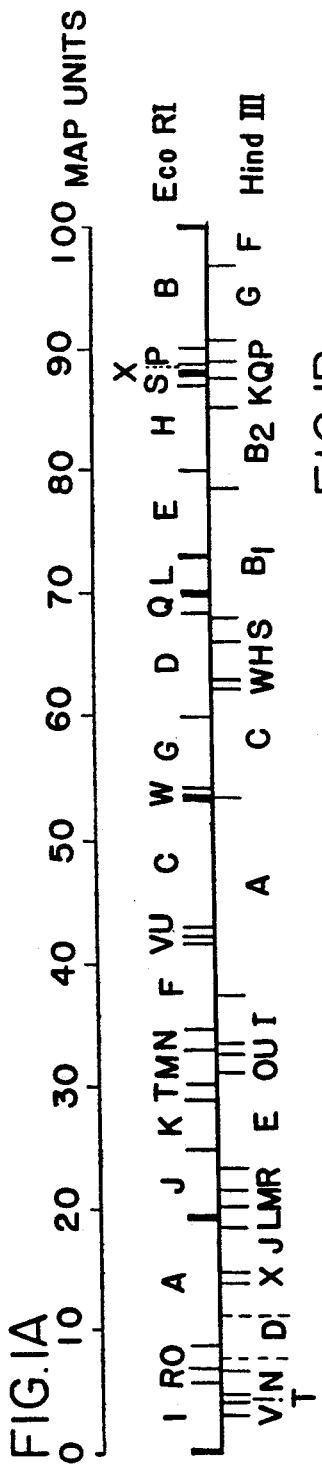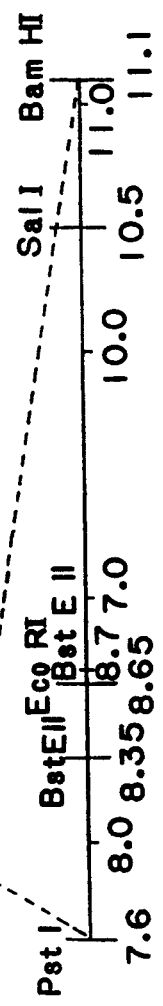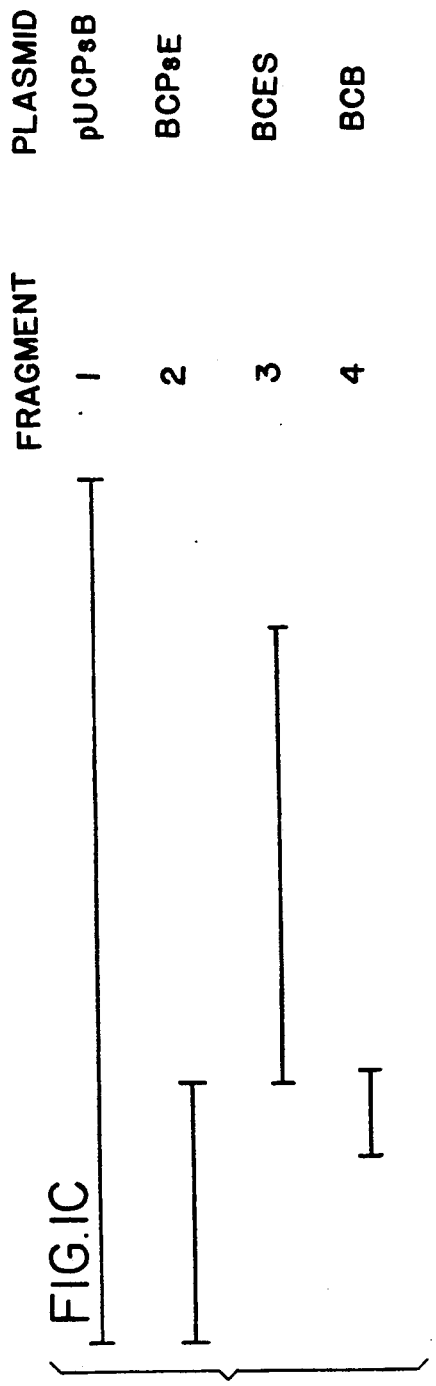

FIG. 3A

```
  1 GTCGACGCGC TTCTGCGTAT AATTGCACAC TAACATGTTG CCCTTTGAAC

51 TTGACCTCGA TTGTGTTAAT TTTTGGCTAT AAAAAGGTCA CCCTTTAAAA

101 TTTGTTACAT AATCAAATTA CCAGTACAGT TATTCGGTTT GAAGCAAAAT
                                                 egt:   M 151 GACTATTCTC TGCTGGCTTG CACTGCTGTC TACGCTTACT GCTGTAAATG
     T  I  L   C  W  L    L  L  S    T  L  T    A  V  N  A 201 CGGCCAATAT ATTGGCCGTG TTTCCTACGC CAGCTTACAG CCACCATATA
     A  N  I   L  A  V    F  P  T    P  A  Y  S   H  H  I 251 GTGTACAAAG TGTATATTGA AGCCCTTGCC GAAAAATGTC ACAACGTTAC
     V  Y  K  V  Y  I  E   A  L  A    E  K  C   H  N  V  T 301 GGTCGTCAAG CCCAAACTGT TTGCGTATTC AACTAAAACT TATTGCGGTA
     V  V  K   P  K  L  F   A  Y  S    T  K  T   Y  C  G  N 351 ATATCACGGA AATTAATGCC GACATGTCTG TTGAGCAATA CAAAAAACTA
      I  T  E   I  N  A    D  M  S  V  E  Q  Y   K  K  L 401 GTGGCGAATT CGGCAATGTT TAGAAAGCGC GGAGTGGTGT CCGATACAGA
     V  A  N  S   A  M  F    R  K  R    G  V  V  S  D  T  D 451 CACGGTAACC GCCGCTAACT ACCTAGGCTT GATTGAAATG TTCAAAGACC
      T  V  T   A  A  N  Y   L  G  L    I  E  M   F  K  D  Q 501 AGTTTGACAA TATCAACGTG CGCAATCTCA TTGCCAACAA CCAGACGTTT
      F  D  N   I  N  V    R  N  L  I   A  N  N   Q  T  F 551 GATTTAGTCG TCGTGGAAGC GTTTGCCGAT TATGCGTTGG TGTTTGGTCA
     D  L  V  V   V  E  A    F  A  D    Y  A  L  V   F  G  H 601 CTTGTACGAT. CCGGCGCCCG TAATTCAAAT CGCGCCTGGC TACGGTTTGG
      L  Y  D   P  A  P  V   I  Q  I    A  P  G    Y  G  L  A 651 CGGAAAACTT TGACACGGTC GGCGCCGTGG CGCGGCACCC CGTCCACCAT
     E  N  F    D  T  V    G  A  V    A  R  H  P   V  H  H 701 CCTAACATTT GGCGCAGCAA TTTCGACGAC ACGGAGGCAA ACGTGATGAC
      P  N  I  W   R  S  N    F  D  D    T  E  A  N  V  M  T 751 GGAAATGCGT TTGTATAAAG AATTTAAAAT TTTGGCCAAC ATGTCCAACG
     E  M  R    L  Y  K  E   F  K  I    L  A  N   M  S  N  A 801 CGTTGCTCAA ACAACAGTTT GGACCCAACA CACCGACAAT TGAAAAACTA
     L  L  K    Q  Q  F    G  P  N  T   P  T  I    E  K  L 851 CGCAACAAGG TGCAATTGCT TTTGCTAAAC CTGCATCCCA TATTTGACAA
     R  N  K   V  Q  L  L   L  L  N    L  H  P  I   F  D  N
```

FIG. 3B

```
 901 CAACCGACCC GTGCCGCCCA GCGTGCAGTA TCTTGGCGGA GGAATCCATC
      N  R  P   V  P  P  S   V  Q  Y    L  G  G    G  I  H  L

951 TTGTAAAGAG CGCGCCGTTG ACCAAATTAA GTCCGGTCAT CAACGCGCAA
      V  K  S   A  P  L    T  K  L  S   P  V  I    N  A  Q

1001 ATGAACAAGT CAAAAAGCGG AACGATTTAC GTAAGTTTTG GGTCGAGCAT
      M  N  K  S   K  S  G    T  I  Y    V  S  F  G   S  S  I

1051 TGACACCAAA TCGTTTGCAA ACGAGTTTCT TTACATGTTA ATCAATACGT
      D  T  K    S  F  A  N   E  F  L    Y  M  L    I  N  T  F

1101 TCAAAACGTT GGATAATTAC ACCATATTAT GGAAAATTGA CGACGAAGTA
      K  T  L    D  N  Y    T  I  L  W   K  I  D    D  E  V

1151 GTAAAAAACA TAACGTTGCC CGCCAACGTA ATCACGCAAA ATTGGTTTAA
      V  K  N  I   T  L  P    A  N  V    I  T  Q  N   W  F  N

1201 TCAACGCGCC GTGCTGCGTC ATAAAAAAAT GGCGGCGTTT ATTACGCAAG
      Q  R  A    V  L  R  H   K  K  M    A  A  F    I  T  Q  G

1251 GCGGACTACA ATCGAGCGAC GAGGCCTTGG AAGCCGGGAT ACCCATGGTG
      G  L  Q    S  S  D    E  A  L  E   A  G  I    P  M  V

1301 TGTCTGCCCA TGATGGGCGA CCAGTTTTAC CATGCGCACA AATTACAGCA
      C  L  P  M   M  G  D    Q  F  Y    H  A  H  K   L  Q  Q

1351 ACTCGGCGTA GCCCGCGCCT TGGACACTGT TACCGTTTCC AGCGATCAAC
      L  G  V    A  R  A  L   D  T  V    T  V  S    S  D  Q  L

1401 TACTAGTGGC GATAAACGAC GTGTTGTTTA ACGCGCCTAC CTACAAAAAA
      L  V  A    I  N  D    V  L  F  N   A  P  T    Y  K  K

1451 CACATGGCCG AGTTATATGC GCTCATCAAT CATGATAAAG CAACGTTTCC
      H  M  A  E   L  Y  A    L  I  N    H  D  K  A   T  F  P

1501 GCCTCTAGAT AAAGCCATCA AATTCACAGA ACGCGTAATT CGATATAGAC
      P  L  D    K  A  I  K   F  T  E    R  V  I    R  Y  R  H

1551 ATGACATCAG TCGTCAATTG TATTCATTAA AAACAACAGC TGCCAATGTA
      D  I  S    R  Q  L    Y  S  L  K   T  T  A    A  N  V

1601 CCGTATTCAA ATTACTACAT GTATAAATCT GTGTTTTCTA TTGTAATGAA
      P  Y  S  N   Y  Y  M    Y  K  S    V  F  S  I   V  M  N

1651 TCACTTAACA CACTTTTAAT TACGTCAATA AATGTTATTC ACCATTATTT
      H  L  T    H  F  *

1701 ACCTGGTTTT TTTGAGAGGG GCTTTGTGCG ACTGCGCACT TCCAGCCTTT

1751 ATAAACGCTC ACCAACCAAA GCAGGTCATT ATTGTGCCAG GACGTTCAAA
```

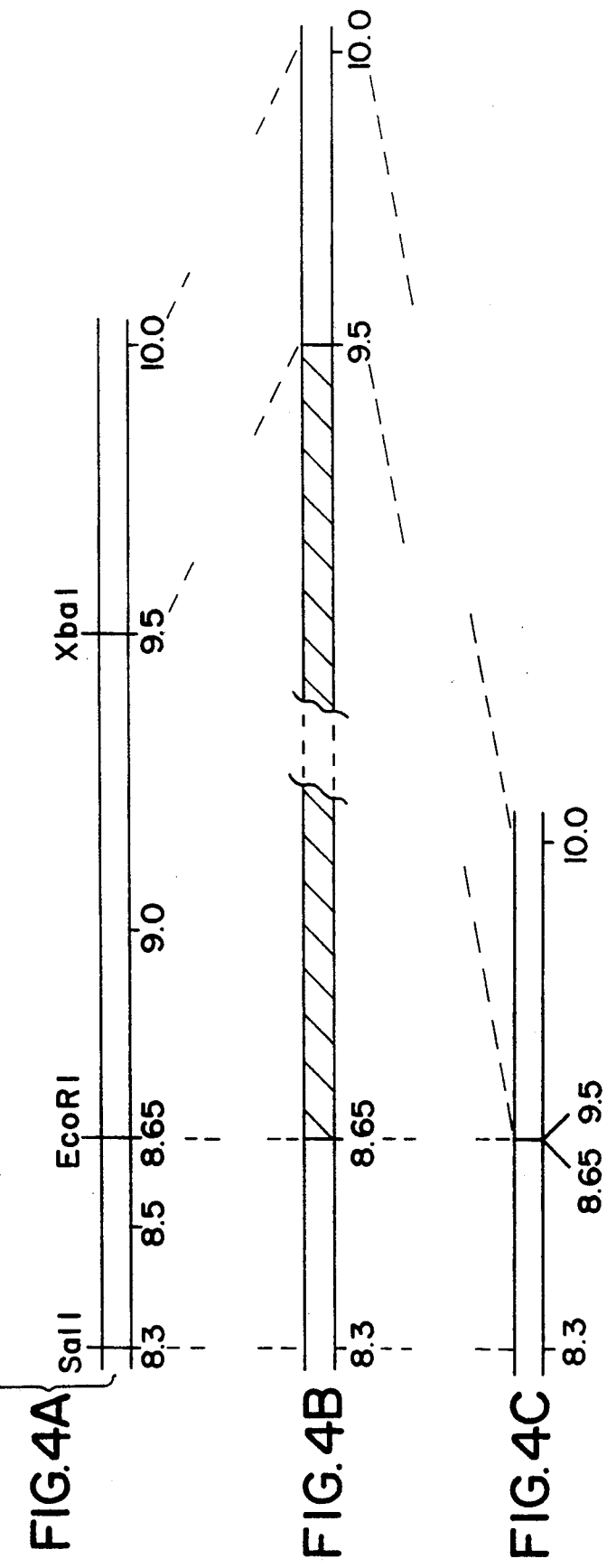

FIG. 6

```
EGT         MTILCWLALLS-----TLTAVNAANILAVFPTPAYSHHIVYKVYIEALAEKCHNVTV
HUMUDPGAT   Msm....ALL........fss.s.gkvL-V.PT-.fSH.m..K..ld.L.qr.HeVTV
MUSUDPGAT   M......ALL........f.sVk.gkvL-V.P.-.fSH.m..Ki.ld.L.qr.HeVTV
RATUDPGAT   M......ALf........f.s.h.gkvL-V.P.-.fSH.m..Ki.ld.L.qr.HeVTV
                                    ↓
EGT         VKP-KLFAYSTKTYCGNITEI-NADMSVE-----QYKKLVANSAMFRKRGVVSDTDT
HUMUDPGAT   l.s...isf..ns......Ev....lt.....-....KqLV...A-...kd......s
MUSUDPGAT   lrP...y....K...G...E....t.vS.d.......K.v...t.-...Rd.......
RATUDPGAT   lKP...F....K...d...EI.st.iS.d.......K.L...t.-...Rd.......

EGT         VTAANYLGLIEMFKDQF-DNINVRNLIANNQ--TFDLVVVEAFADYALVFGHLYDPA
HUMUDPGAT   ........f.dilr....D.vs.kkLm.k.Q...FDvVl.dAl..fg.llaeL...p
MUSUDPGAT   l.......f.d.F.....D.vs.keLmtk.Q...FDvll.dpiA..g.liaeL.q.p
RATUDPGAT   i.......f...y.....D.vs.kqLmtk.Q...FDvl..dpiA..g.liaeL.h.p EGT         PVI--QIAPGYGLAENFDTVGAVAR-HPVHHPNIW-RSNFDDTEANVMTEMRLYKEF
HUMUDPGAT   .V....rfsPGYai..h.g.l...p...PV..sel..q..F.e...Nmi-.v-LY.EF
MUSUDPGAT   .l....rfsPGY.i..s.g.....p...PV..s.l..q..F.e...Nmi-.M-LY.dF
RATUDPGAT   .l....fsPG..L..sig.....p...PV..s.l..k..F.D...Nmi-.M-LY.dF EGT         --KIL-ANMSNALLKQQFGPNTPTIEKLRNKVQLLLLNLHPIFDNNRPVPPSVQYLG
HUMUDPGAT   ..qIf..k..d.f..e.lG..T-Tl.....K.di.Li.....Fq..hPl.PnVefv-
MUSUDPGAT   ..qmf..k..dsf..e.lG..T-Tl.....q.em.Li..n..le..hP..PnVdYv-
RATUDPGAT   ....L..k..dtf..e.lG..T-Tvd...sKVei.Li.....l...hP..PnVdYi- EGT         GGIHLVKSAPLTKLSPVINAQMNKSKSGTIYVSFGSSIDTKSFANEFLYMLINTFKT
HUMUDPGAT   GGlH...a.PL.K....f-.Q.s..ng..vf-SlGS.v-.-n.seE...vi.sal..
MUSUDPGAT   GGlH...a.PL.K....f-.Q.s...g..vf-SlGS.v-.-n.teE....i..al..
RATUDPGAT   GGlH...a.PL.K....f-.Q.s...g..vf-SlGS.v-.-n.teE....L..al..
ZMAYUDPGT                     285   qp..G..YVSFGT....rp...El...L.ds...

EGT         LDNYTILWKIDDEVVKNITLPANVITQNWFNQRAVLRHKKMAAFITQGGLQSSDEAL
HUMUDPGAT   i.-..vLWrfDgn.....l.L.t.l--..kWi.Q...lL.H.K..AFIThGG.ng...Ai
MUSUDPGAT   i.-..vLWKfDg.....l...t.V--..kWl.Q...lL.H.K..AFhThGG.ng...EAi
RATUDPGAT   i.-..vLWKfDg.....l...t.V--..kWl.Q...lL.H.K..AFvThGG.ng..EAi
ZMAYUDPGT   L......W.l....l...a..g..l...W..Q.AVLRH..vgAFvThaG..S..EgL

EGT         EAGIPMVCLPMMGDQFYHAHKLQQLGVARALDTVTVSSDQLLVAINDVLFNAPTYKK
HUMUDPGAT   .p.IPMV.vPl.aDQ..n...mk..G.A.sLD..TmSS.dLL.Alk.Vi-N.P.YK.
MUSUDPGAT   ..GIPMi.iPl.GeQ..n...m...G.A.ALn..TmS..dvL.AleeVi-..P.YKK
RATUDPGAT   ..GIPMi.iPl.GDQ..n...m...G.A.sLn..TmS..dfL.AleeVi-d.P.YKK
ZMAYUDPGT   .sGvPM.C.P..GDQ..nAr.v.hvG.G.Afe.-amtS..v..AveelL......rr
                                    ↓
EGT         HMAELYALINHDKATFPPLDKAIKFTERVIRYRHDISRQLYSLKTTAANVPYSNYYM
HUMUDPGAT   n...L-s.IhHDqp-..PLDrA-.F....v-.RH..akhL...---A.dl.---.f.
MUSUDPGAT   n...L-s.IhHDqp-..PLDrA-.F....v-.RH..akhL.pL---g.Nl.---.f.
RATUDPGAT   nv..L-s.IhHDqp-..PLDrA-.F....I-.RH..akhL.pL---g.NlP---.Y.
ZMAYUDPGT   ..AEL.ALv.e..g......K.frF.E.V.R.

EGT         YKSVFSIVMNHLTHF*
HUMUDPGAT   Y.S-l.v....La...............-...............*
MUSUDPGAT   Y.S-l.vi...Ls................................*
RATUDPGAT   Y.S-l.vi...LT.F..............................*
```

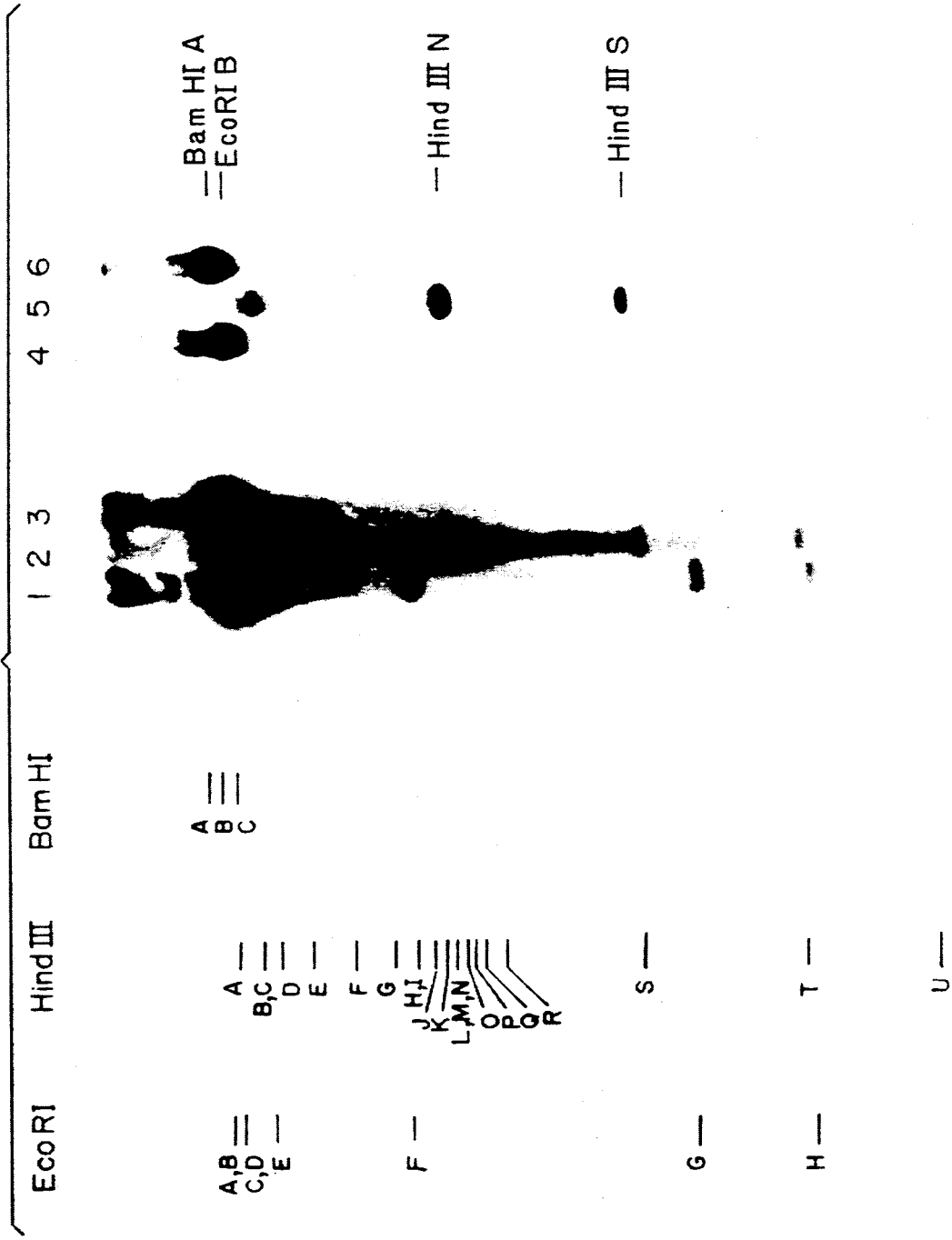

BIOLOGICAL INSECT CONTROL AGENTS AND METHODS OF USE

This invention was made with funding from the National Institutes of Health (Grant No. AI-23719) and with Hatch Act funding from the U.S. Department of Agriculture (Grant No. GE000918). The U.S. government may have certain rights in this invention.

TECHNICAL FIELD

The present invention relates to methods and compositions for improved biological control of insect pests. More particularly, the present invention relates to the use and manipulation of a gene and its gene product which are effective in controlling the growth and development of insects. The present invention also relates to genetically modified viruses that adversely affect infected insects.

BACKGROUND OF THE INVENTION

Interest in the biological control of insect pests has arisen as a result of the problems associated with the use of conventional chemical pesticides. Chemical pesticides generally affect beneficial as well as non-beneficial species. Pest insects tend to acquire resistance to such chemicals so that new pest insect populations can rapidly develop that are resistant to these pesticides. Furthermore, chemical residues pose environmental hazards and possible health concerns. The biological control of insect pests presents an alternative means of pest control which can play a role in integrated pest management and reduce dependence on chemical pesticides.

The primary strategies for biological control include the deployment of naturally occurring organisms which are pathogenic to insects (entomopathogens), and the development of crops that are more resistant to insect pests. In recent times, much attention has been focused on the development of insect-resistant crop species by genetic engineering techniques. There is considerable potential for the improvement of biological control strategies through a variety of approaches. These include the identification and characterization of insect genes or gene products which may serve as suitable targets for insect control agents, the identification and exploitation of previously unused microorganisms (including the modification of naturally occurring nonpathogenic microorganisms to render them pathogenic to insects), the modification and refinement of currently used entomopathogens, and the further development of genetically engineered crops which display greater resistance to insect pests.

Viruses that cause natural epizootic diseases within insect populations are among the entomopathogens which have been developed as biological pesticides. Baculoviruses are a large group of viruses which are infectious only in arthropods (L. K. Miller, Virus Vector for Genetic Engineering in Invertebrates, in "Genetic Engineering in the Plant Sciences", N. Panopoulous, Ed., Praeger Publ., N.Y., pp. 203-224, 1981; Carstens, "Baculoviruses—Friend of Man, Foe of Insects?," *Trends and Biochemical Science*, 52:107-110, 1980; Harrap and Payne, "The Structural Properties and Identification of Insect Viruses" in *Advances in Virus Research*, M. A. Lawfer, F. B. Bang, K. Maramorosh and K. M. Smith, Eds., Vol. 25, pp. 273-355, Academic Press, New York, 1979). Many baculoviruses infect insects which are pests of commercially important agricultural and forestry crops. Such baculoviruses are therefore potentially valuable as biological control agents. In fact, four different baculoviruses have been registered for use as insecticides by the U.S. Environmental Protection Agency. Among the advantages of baculoviruses as biological pesticides is their host specificity. Not only are baculoviruses as a group found solely in arthropods, individual baculovirus strains are usually restricted in their replication to one or a few species of insects. Thus, they pose no risk to man or the environment and can be used without detriment to beneficial insect species.

Baculovirus subgroups include nuclear polyhedrosis viruses (NPV), granulosis viruses (GV), and nonoccluded baculoviruses. In occluded forms of baculoviruses (NPV and GV subgroups), the virions (enveloped nucleocapsids) are embedded in a crystalline protein matrix. This structure, referred to as an inclusion or occlusion body, is the form found extraorganismally in nature and is responsible for spreading the infection between organisms. The characteristic feature of viruses of the subgroup NPV is that many virions are embedded in each occlusion body. The occlusion bodies are quite large (up to 5 micrometers). Occlusion bodies of viruses of the GV subgroup are smaller and contain a single virion each. The crystalline protein matrix of the occlusion bodies of both forms is primarily composed of a single 25,000 to 33,000 dalton polypeptide which is known as polyhedrin or granulin. Baculoviruses of the nonoccluded subgroup do not produce a polyhedrin or granulin protein and do not form occlusion bodies.

In nature, infection is initiated when an insect ingests food contaminated with baculovirus particles, typically in the form of occlusion bodies. The occlusion bodies dissociate under the alkaline conditions of the insect midgut, releasing individual virus particles which invade epithelial cells lining the gut. Within the cell, the baculovirus migrates to the nucleus where replication takes place. Initially, certain specific viral proteins are produced within the infected cell via the transcription and translation of so-called "early genes". Among other functions, these proteins are required to allow replication of the viral DNA, which begins 4 to 6 hours after the virus enters the cell. Extensive viral DNA replication proceeds up to about 12 hours post-infection (pi). From about 8 to 10 hours pi, the infected cell begins to produce large amounts of "late viral gene products". These include components of the nucleocapsid which surround the viral DNA during the formation of progeny virus particles. Production of the progeny virus particles begins around 12 hours pi. Initially, progeny virus migrate to the cell membrane where they acquire an envelope as they bud out from the surface of the cell. This nonoccluded virus can then infect other cells within the insect. Polyhedrin synthesis begins from 12 to 18 hours after infection and increases to very high levels by 24 hours pi. At that time, there is a decrease in the number of virus particles budding from the cell and progeny virus begin to become embedded in occlusion bodies. Occlusion body formation continues until the cell ultimately dies or lyses. Some baculoviruses infect virtually every tissue in the host insect so that at the end of the infection process, the entire insect is liquified, releasing extremely large numbers of occlusion bodies which are then responsible for spreading the infection to other insects. (Reviewed in: "The Biology of Baculoviruses," R. G. Granados and B. A. Federici, Eds., Vol. I and II, CRC Press, Boca Raton, Fla., 1986.)

One of the significant disadvantages to using baculoviruses as pesticides is the length of time which elapses between ingestion of the virus and the time the insect finally dies. During this time, the pest insect will continue to feed and damage the crop. Because the grower is unlikely to apply the pesticide until after an infestation becomes apparent, it is critical that the extent of feeding during this lag period be kept to a minimum.

What is needed is a biological pesticide which reduces the the adverse effects of the pesticide. A biological pesticide is preferred because it creates less of an environmental hazard than a chemical pesticide. A pesticide that causes insect death more rapidly is additionally needed. What is also needed is the identification and isolation of a gene that codes for a protein which will control insect development. Such a gene or its protein product could then be incorporated into various organisms for the improved biological control of insect pests.

SUMMARY OF THE INVENTION

The present invention comprises a newly identified gene and its gene product which affect the growth, development or behavior of insects. The present invention also includes methods for the use of this gene or gene product, as well as methods for the inactivation of this gene or its gene product in insect control strategies. The gene encodes for an edysteroid-modifying enzyme, preferably ecdysteroid UDP-glucosyl transferase (EGT). Expression of the egt gene causes the production of EGT which then inactivates insect molting hormones and prevents the insect from molting or pupating. Inactivation of the egt gene allows molting and pupation to proceed.

The present invention encompasses a broad range of insect control agents utilizing the egt gene and its gene product. The insect control agents of the present invention either cause the inappropriate synthesis of (EGT) or prevent the normal functioning of (EGT) in the insect pest. Both the production of EGT at an inappropriate time or the absence of (EGT) when it is required will interfere with the development of the insect pest.

Preferably, the organism containing the egt gene comprises a virus specific for the insect pest wherein the aforementioned gene of the virus is inactivated, thereby allowing the continued development of the insect host infected with the virus. Development of the insect host induces behavioral changes such as reduced feeding and, in conjunction with infection by the viral pesticide, causes reduced growth and more rapid death. The present invention also includes a method for producing the improved viral pesticide. In addition, the present invention includes a method of controlling insect pests comprising exposing the insect pest to the viral pesticide.

The genetically altered viruses contemplated by the present invention are more efficient pesticides than prior art viruses. Baculoviruses, such as *Autographa californica* nuclear polyhedrosis virus (AcMNPV) and *Orgyia pseudotsugata* nuclear polyhedrosis virus (OpMNPV), express an egt gene which prolongs the period of time an infected larva spends feeding before succumbing to the viral infection. The present invention includes inactivating the egt gene in the genome of viruses such as, but not limited to, baculoviruses. The egt gene can be inactivated by substituting in its place another gene such as, but not limited to, the non-viral marker gene for $\beta$-galactosidase. It should be understood that any DNA sequence could be used to disrupt the egt gene as long as it disrupts the egt coding sequence. Alternatively, all or part of the egt gene can be removed from the genome by deleting the appropriate DNA segment or the regulatory part of the genome that controls the egt gene can be altered or removed. The resulting virus has the advantage that it contains no foreign genes and only differs from wild-type virus in that it lacks the egt gene. Such modified baculoviruses function better as pest control agents than the viruses presently in use. As simple deletion mutants, they should also be acceptable to regulatory agencies (e.g. U.S. EPA) as genetically engineered pesticides. Baculoviruses that do not express a functional egt gene are modified by the insertion of genes other than egt which interfere with insect development. The efficiency of such viruses as insect control agents is thus improved.

The present invention also includes a method of infecting an insect larvae with a mutant virus lacking an intact egt gene or incapable of expressing a functional EGT product. The mutant virus-infected larvae attempt to molt and pupate and consequently feed for a shorter period of time than larvae infected with wild-type or other prior art viruses. The mutant virus-infected insect larvae also die sooner than wild-type or other prior art virus-infected larvae.

The present invention includes a recombinant baculovirus, designated vEGTZ, in which a portion of the egt gene has been deleted and replaced by lacZ, a bacterial gene encoding the enzyme $\beta$-galactosidase. The present invention also includes a recombinant baculovirus, designated vEGTDEL, in which a portion of the egt gene has been deleted.

Accordingly, it is an object of the present invention to provide a gene and its gene product that are useful in the control of insect pests.

It is another object of the present invention to provide a recombinant virus that is a more effective pesticide than the wild-type virus.

It is yet another object of the present invention to provide a recombinant baculovirus that is a more effective pesticide than prior art baculoviruses.

It is yet another object of the present invention to provide a genetically engineered virus that is an effective pesticide and is also environmentally acceptable.

It is yet another object of the present invention to provide a baculovirus pesticide in which the egt gene has been replaced by another gene.

It is yet another object of the present invention to provide a baculovirus pesticide in which the egt gene has been replaced by a $\beta$-galactosidase gene.

It is yet another object of the present invention to provide a recombinant baculovirus pesticide that lacks an egt gene and expresses a second gene which interferes with insect development.

It is yet another object of the present invention to provide a modified biological pesticide that expresses a genetically inserted egt gene.

It is another object of the present invention to provide a modified biological pesticide that interferes with the egt gene or gene product.

It is another object of the present invention to provide a baculovirus pesticide in which the egt gene has been removed.

BRIEF DESCRIPTION OF THE DRAWINGS

FIG. 1 is a schematic representation of the AcMNPV genome showing the location of the egt gene.

FIG. 3 is a schematic representation of the nucleotide sequence and the predicted amino acid sequence of the egt gene.

FIG. 4 is a schematic representation of the structures of the egt gene regions of AcMNPV (Panel A) and the recombinant viruses vEGTZ (Panel B) and vEGTDEL (Panel C). The hatched box represents the lacZ gene.

FIG. 6 is a schematic diagram comparing the alignment of the EGT amino acid sequence with a selection of UDP-glucuronosyl transferases and a UDP-glucosyl transferase from other species. The predicted amino acid sequence of EGT is compared to human (HUMUDPGAT), (M. R. Jackson et al., *Biochem. J.*, 242:581, 1987), mouse (MUSUDPGAT), (T. Kimura and I. S. Owens, *Eur. J. Biochem.*, 168:515, 1987), and rat (RATUDPGAT) (P. I. MacKenzie, *J. Biol. Chem.*, 262:9744, 1987), UDP-glucuronosyl transferases as well as maize UDP-glucosyl transferase (ZMAYUDPGT), (E. J. Ralston, J. J. English, H. K. Doone, *Genetics*, 119:185, 1988), using the FASTP algorithm, (D. J. Lipman and W. R. Pearson, *Science*, 227:1435, 1985), as implemented by International Biotechnologies Inc. Upper case letters denote exact matches; lower case letters denote substitutions which occur frequently among related proteins, (M. Dayhoff, Atlas of Protein Sequence and Structure, National Biomedical Research Foundation, Vol. 5, Supplement 3, Silver Spring, Md., 1978); dots represent substitutions which occur infrequently; hyphens indicate gaps in a sequence; and a caret marks where an amino acid has been deleted from the sequence. The amino acids between the arrows are deleted from the egt gene in vEGTZ and vEGTDEL.

FIG. 8 is a schematic representation of an electrophoretic gel and Southern blot analysis for identification of an egt gene in the baculovirus OpMNPV.

DETAILED DESCRIPTION OF THE DISCLOSED EMBODIMENTS

Lepidopteran insects undergo a well characterized sequence of events during development from egg to adult insect (see "Comprehensive Insect Physiology, Biochemistry and Pharmacology," G. A. Kerkut and L. I. Gilbert, Eds., Vols. 7 and 8, Pergamon Press, Oxford, 1984, for detailed reviews). After hatching, the insect larva enters a period of extensive feeding during which time it will molt several times to allow continued growth. Stages between successive molts are known as instars. At the end of the larval growth period, the larva pupates and finally emerges as an adult insect. The processes of molting and pupation (collectively termed ecdysis) are regulated by the concerted actions of several different groups of hormones. The initial stimulus is the release of prothoracicotropic hormone (PTTH) by certain brain cells. This stimulates the prothoracic glands to produce and secrete ecydsteroids, often referred to as insect molting hormones. In the presence of juvenile hormone, a larval molt will ensue, while in the absence of juvenile hormone the larvae will pupate. Eclosion hormone is also important in mediating several behavioral changes associated with ecdysis.

The present inventors have discovered that the baculovirus *Autographa californica* nuclear polyhedrosis virus (AcMNPV), which is used as a model system for much baculovirus research, interferes with the process of insect development discussed above in a remarkable and previously unsuspected manner. The present inventors have shown that insect larvae infected with AcMNPV are no longer able to molt or pupate. They have demonstrated that this is because AcMNPV directs the synthesis of an enzyme, known as ecdysteroid UDP-glucosyl transferase (EGT), which specifically inactivates the insect ecdysteroids.

Figure 2A:
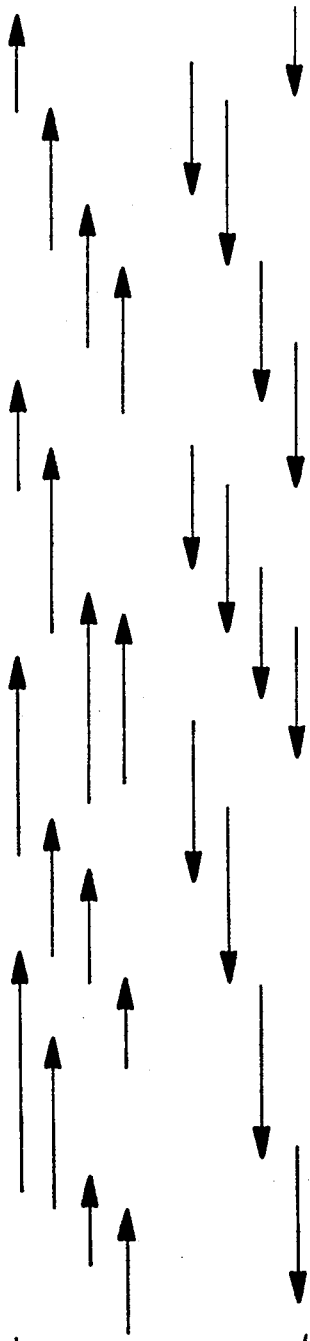
FIG. 2 is a schematic representation of the strategy used to sequence the egt gene and the analysis of the sequence obtained. The arrows in panel A represent the extent of sequence determined from each subclone. Panel B depicts a map of the region. The results of the computer-assisted translation of the sequence obtained are shown in Panel C. The vertical lines indicate stop codons. The sequence is translated in all six open reading frames (1, 2, 3, 1', 2', 3').
Figure 2B:
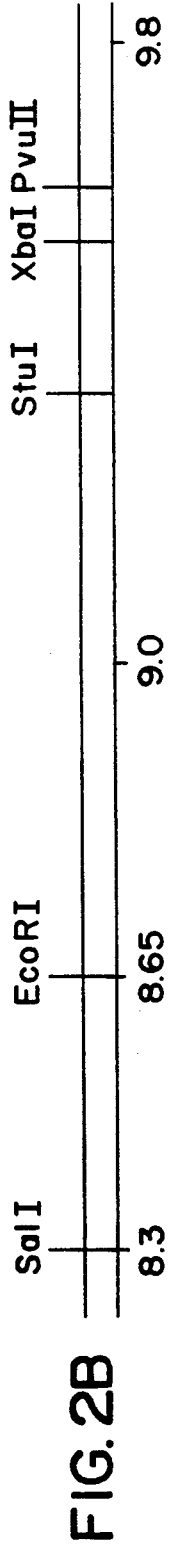
Figure 2C:
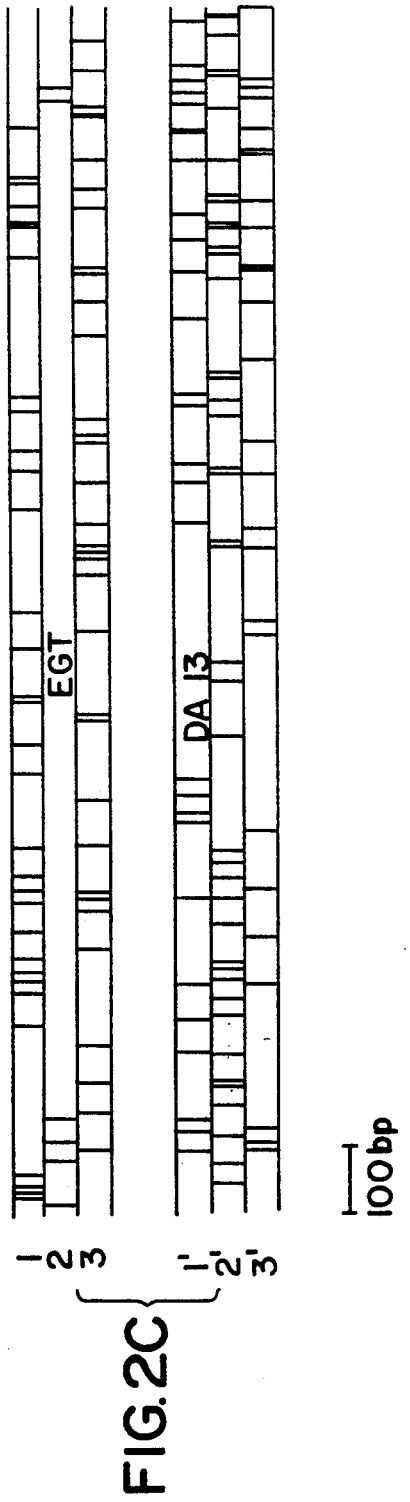

The gene encoding egt, as identified by the present inventors, extends from 8.4 to 9.6 map units on the AcMNPV genome as shown in FIG. 1. As shown in Panel C of FIG. 1, viral DNA encompassing the egt gene has been cloned into the plasmids pUC19, Bluescript M13+, Bluescript M13−. The nucleotide sequence of this gene has been determined and indicates that the gene can encode a protein of 506 amino acids as shown in FIGS. 2 and 3.

Figure 5:
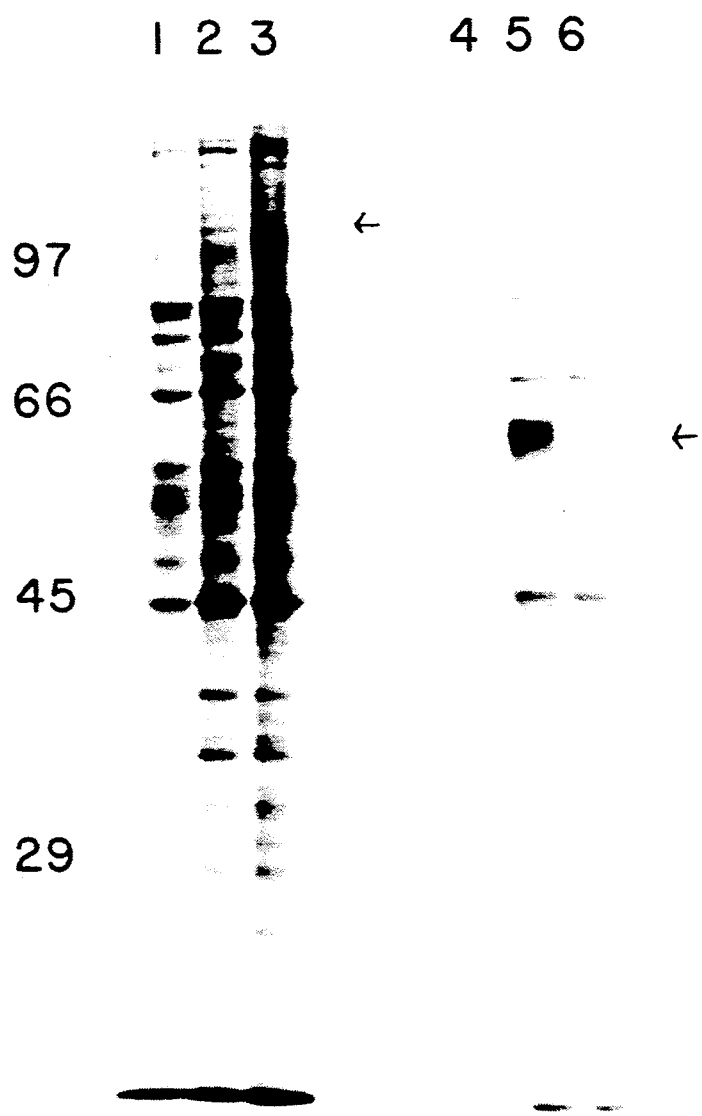
FIG. 5 is a copy of a photograph of an electrophoretic gel subjected to autoradiography which illustrates the identification of the EGT protein. [$^{35}$S]methionine labeled proteins from uninfected (lanes 1 and 4), wt AcMNPV-infected (lanes 2 and 5), and vEGTZ-infected (lanes 3 and 6) cells (lanes 1 to 3) and extracellular media (lane 3 to 6) are analyzed by SDS-PAGE. The arrows indicate the egt-$\beta$-galactosidase fusion protein in lane 3 and the EGT protein in lane 5.

In the first preferred embodiment of the present invention, a portion of the egt gene of the baculovirus AcMNPV is modified by replacing that portion with the bacterial gene encoding $\beta$-galactosidase. This recombinant baculovirus is designated vEGTZ. In the second preferred embodiment, designated vEGTDEL, part of the egt gene is modified by removing that portion without replacement, as shown in FIG. 4. As shown in FIG. 5, a comparison of the proteins synthesized during wt AcMNPV and vEGTZ infection reveal that the (EGT) protein is a 60,000 Dalton protein which is secreted from infected cells.

A search of the Genbank database revealed 21 to 22% amino acid sequence identity between EGT and several mammalian UDP-glucuronosyl transferases.

Homology was also found to a plant UDP-glucosyl transferase. The alignment of the EGT amino acid sequence with a selection of these enzymes is displayed in FIG. 6. In mammals, the UDP-glucuronosyl transferases catalyze the transfer of glucuronic acid to a wide variety of both exogenous and endogenous lipophilic substrates (Reviewed in: "Glucuronidation of Drugs and other Compounds," G. J. Dutton, Ed., CRC Press, Boca Raton, Fla., 1986). This conjugation reaction is of critical importance in the detoxification and safe elimination of a multitude of drugs and carcinogens. In addition, the normal metabolism and disposal of various endogenous compounds such as bilirubin and steroid hormones, proceed via their conjugation with glucuronic acid. Available evidence on insect systems indicate that sugar conjugation reactions of this type involved glucose rather than glucuronic acid transfer (Reviewed in: J. N. Smith, In "Drug Metabolism-From Microbe to Man," D. V. Parke and R. L. Smith, Eds., Taylor and Francis Ltd., London, pp. 219-232, 1977). As in mammals, a wide variety of both exogenous and endogenous compounds are prone to conjugation.

Figure 7A:
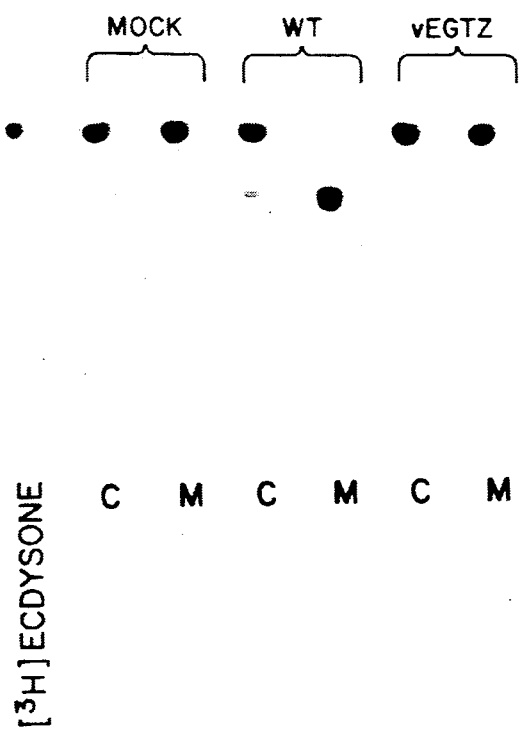
FIG. 7 is a schematic represention showing the presence of absence of EGT activity in cell lysates (C) and overlying medium (M) of cells infected with wt AcMNPV, vEGTZ and uninfected (mock) cells.
Figure 7B:
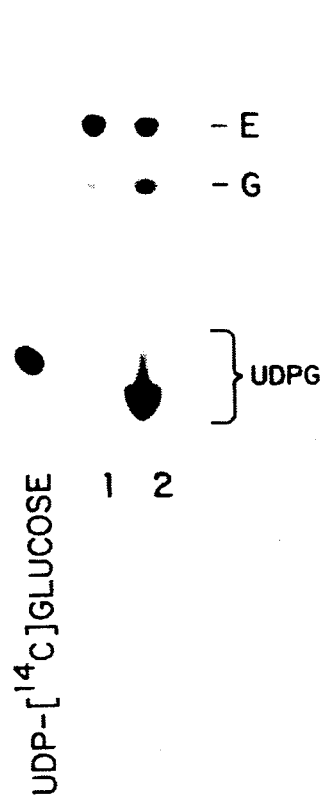

Through a series of experiments, the inventors have shown that the EGT protein is a UDP-glucosyl transferase which specifically conjugates glucose with ecdysteroids such as ecdysone, 20-hydroxyecdysone and makisterone A (see Table 1 below and FIG. 7). These experiments have revealed that the EGT enzyme is secreted into the extracellular medium by AcMNPV-infected cells. Using the AcMNPV egt gene as a probe, an egt gene has been identified in another baculovirus, *Orgyia pseudotsugata* nuclear polyhedrosis virus (OpMNPV) as shown in FIG. 8. It will be recognized by those skilled in the art with the benefit of this disclosure that the egt gene of any baculovirus, insect virus or insect can be located and characterized in a similar manner.

By comparing the properties of vEGTZ with the properties of wild-type (wt) AcMNPV, the present inventors have shown that expression of egt by the virus prevents the insect from molting or pupating. Insects infected with wt AcMNPV do not molt or pupate. However, insects infected with vEGTZ, in which the egt gene is nonfunctional, are able to molt and also attempt to pupate (see Table 2 in Example II below).

Figure 10:
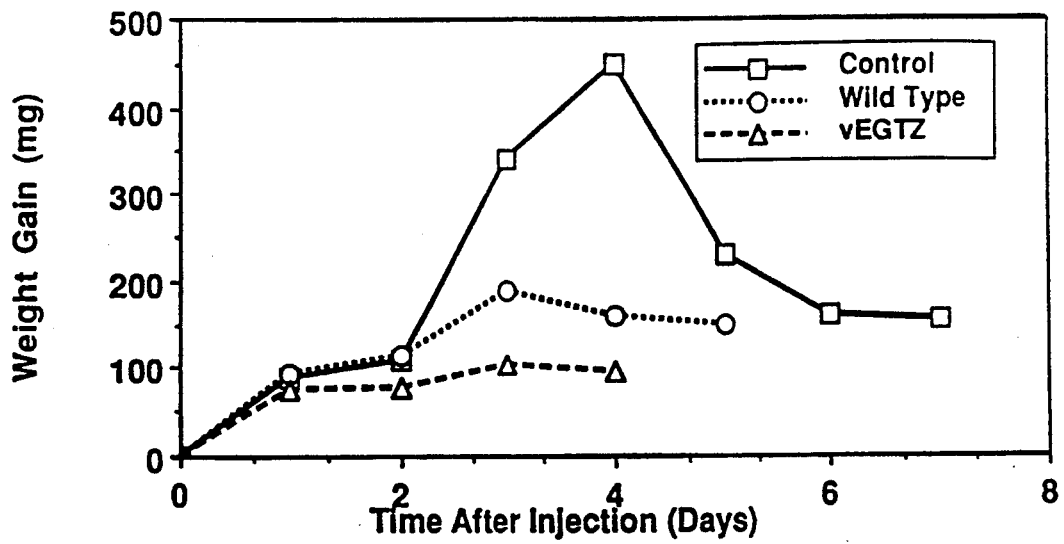
FIG. 10 is a graph of the weight gain after infection of larvae at 4th instar with wt AcMNPV or vEGTZ.

The present inventors have also discovered that, by inhibiting molting and pupation, wt AcMNPV infection can actually prolong the length of time the larva spends feeding. Larvae infected at the beginning of fifth instar (the last larval instar) with wt virus do not die until 5 or 6 days after infection. They continue feeding up to this time. However, larvae which have not been infected stop feeding 2 to 3 days after entering fifth instar in preparation for pupation (see FIG. 12). Similar effects are observed when larvae at earlier instars are examined. Uninfected larvae cease feeding for approximately 24 hours during the molt, while larvae infected by wt AcMNPV do not molt and consequently do not stop feeding (see FIG. 10).

Figure 11:
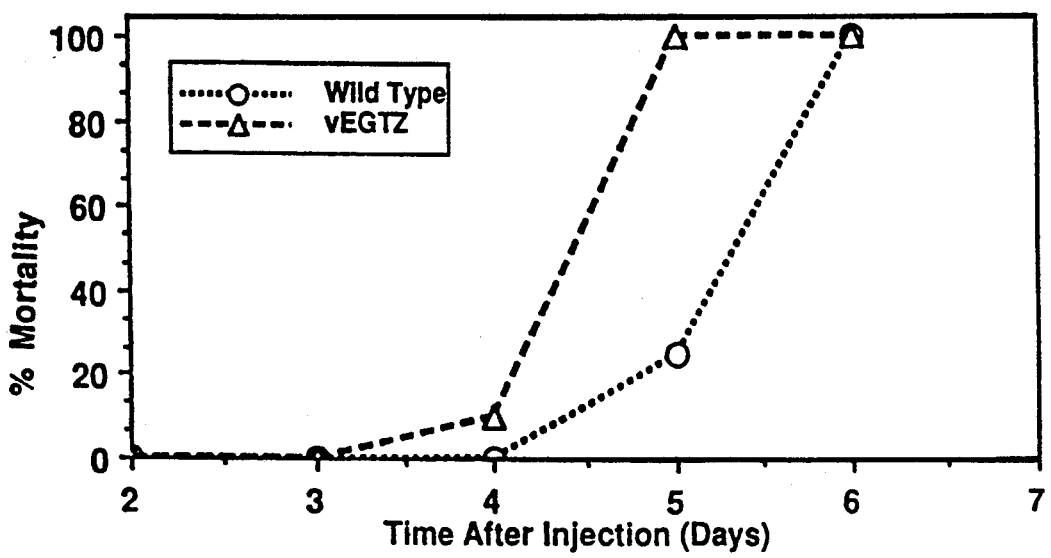
FIG. 11 is a graph of larval mortality after infection of larvae at 4th instar with wt AcMNPV or vEGTZ.
Figure 14:
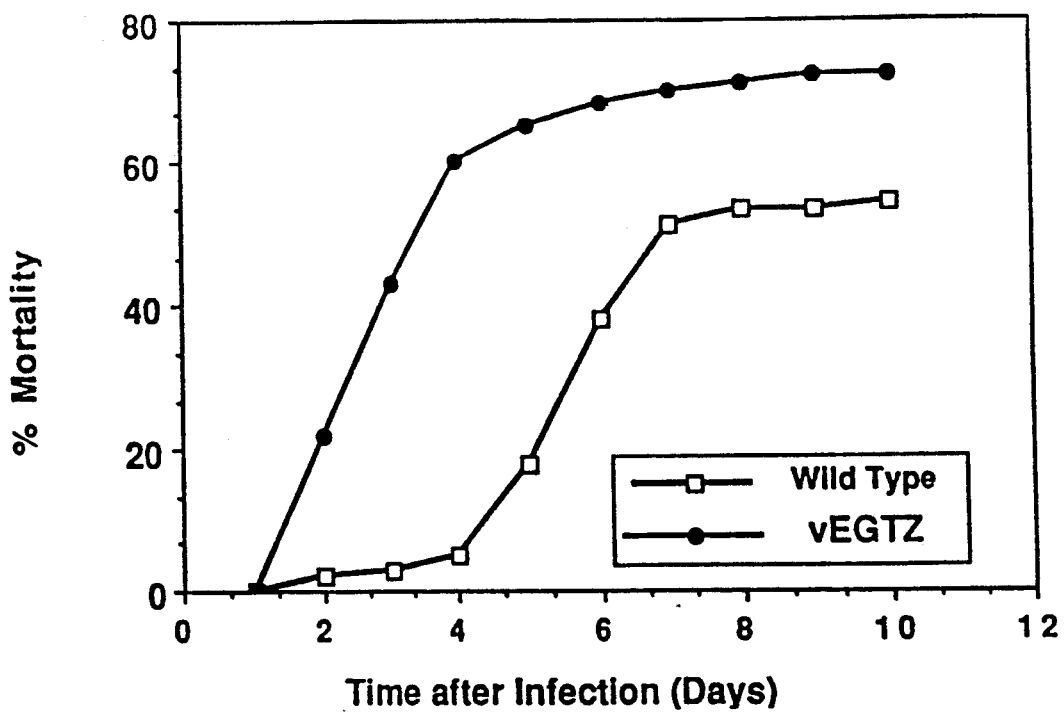
FIG. 14 is a graph of larval mortality after infection of larvae at first instar with wt AcMNPV or vEGTZ at a concentration of $4.8 \times 10^6$ polyhedral inclusion bodies (PIB)/ml.
Figure 15:
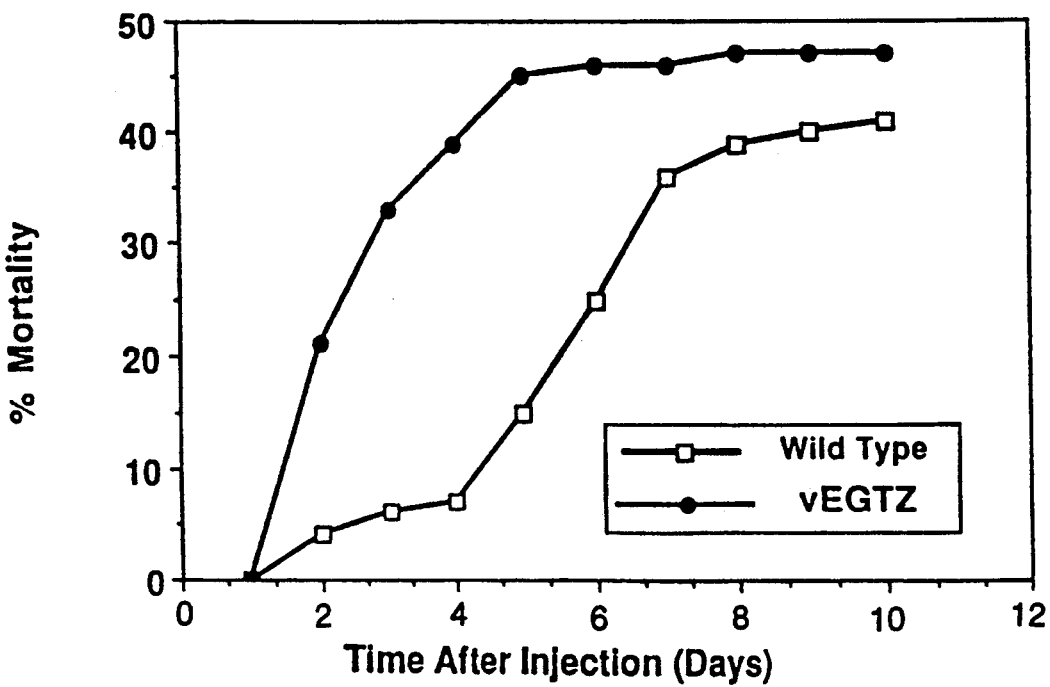
FIG. 15 is a graph of larval mortality after infection of larvae at first instar with wt AcMNPV or vEGTZ at a concentration of $2.4 \times 10^6$ PIB/ml.

The inventors' experiments have shown that recombinant baculoviruses which lack a functional egt gene do not prolong the length of time the larva spends feeding. Thus, larvae infected with vEGTZ at early fifth instar cease feeding two days after infection in preparation for pupation (see FIG. 12). However, they do not pupate and instead succumb to the viral infection even more rapidly than larvae infected with wt virus, as shown in FIG. 13. Similarly, larvae infected with vEGTZ early in fourth instar cease feeding two days after infection to molt, and then die more rapidly than wt-infected larvae (see FIGS. 10 and 11). The more rapid killing by a baculovirus lacking a functional egt gene is most dramatically seen when newly hatched first instar larvae are infected with wt AcMNPV and with vEGTZ as shown in FIGS. 14 and 15. Larvae infected with vEGTZ succumb to the viral infection 3 to 4 days sooner than larvae infected with wt AcMNPV. Therefore, recombinant baculoviruses lacking a functional egt gene will be considerably more effective than the wild-type baculovirus as insect control agents. It will be apparent to those skilled in the art with the benefit of this disclosure that the egt gene can be rendered non-functional in any baculovirus or insect virus in a manner similar to that described herein.

It is believed that the effects described above and in the following examples will be even more dramatic in the field. vEGTZ-infected larvae appear to have some difficulty in molting and do so successfully only under carefully controlled laboratory conditions. When temperature and light are not rigorously controlled, many insects fail to complete the molt. These insects do not recommence feeding and die shortly thereafter.

Although the length of time progeny virus can accumulate in larvae infected with baculoviruses lacking a functional egt gene is somewhat truncated, and the infected insect displays reduced growth, there is nevertheless substantial production of progeny virus. The amount of virus obtained per larva following vEGTZ infection of late instar larvae is approximately half that obtained with wt virus. This is ample to allow transmission of the virus in the field and cost-effective preparation of large quantities of virus particles.

In a third embodiment of the present invention, an insect virus lacking a functional egt gene is modified by genetic engineering techniques so that its effectiveness as a biological control agent is enhanced as described below.

The gene encoding PTTH (a peptide hormone) can be inserted into the viral genome from which the egt gene has been deleted such that it is expressed at high levels. Insect larvae infected with such a virus will experience extreme disruption in the hormonal control of their development. These insects will attempt to molt prematurely, resulting in severely compromised growth and development, reduced feeding, and earlier death.

Eclosion hormone is also a small peptide hormone whose gene can be inserted into the viral genome, from which the egt gene has been deleted, in a similar manner. Because occlusion hormone governs many of the behavioral changes associated with ecdysis, insects infected by a virus producing high levels of this hormone may display various behavioral abnormalities including reduced feeding.

The level of active juvenile hormone in the insect hemolymph is the principal determinant of whether the insect undergoes a larval or pupal molt. When juvenile hormone levels are below a certain threshold, the insect will pupate at the next ecdysis. One of the prime regulators of juvenile hormone titers in the insect is the enzyme juvenile hormone esterase, which inactivates juvenile hormone. A recombinant virus can be produced which expresses high levels of juvenile hormone esterase. Insects infected with this virus will attempt to pupate at the next ecdysis, regardless of their stage of development, because active juvenile hormone titers will be extremely low. Such insects will therefore only survive to the end of the instar during which they become infected.

It is important to note that, while all of the above genes could be expressed in wild-type virus, they would not be expected to affect insect behaviour in a significant manner. This is because expression of the egt gene by wild-type virus inactivates the ecdysteroid molting hormones and ecdysis is prevented, regardless of the production of other hormones. Thus, the success of strategies involving the generation of viruses designed to interfere with insect ecdysis is dependent upon the prior inactivation of the egt gene, as described in this invention. It will be understood by those skilled in the art that mutant organisms lacking an intact egt gene or incapable of expressing a functional EGT product are included as insect control agents of the present invention.

The egt gene product has been shown to interfere with insect development in a powerful and specific manner. Ecdysteroids play a critical role in the development of essentially all insect species (Reviewed in: "Comprehensive Insect Physiology Biochemistry and Pharmacology, " G. A. Kerkut and L. I. Gilbert, Eds. Pergamon Press, Oxford, 1984). Thus, EGT itself has considerable potential for use in broad-based insect control strategies. For example, in a fourth preferred embodiment of the present invention, crop species are genetically engineered so that they constitutively produce the EGT protein. Insects feeding upon such crops will not be able to complete their development to adult insects, providing effective long-term protection for the crop. Similarly, bacteria normally present in the plant or insect can be genetically engineered to produce the EGT enzyme. Such bacteria will function as effective biological control agents.

It is likely that insects themselves express an egt gene at specific stages during their life cycle and that this constitutes an important component of the mechanisms regulating their development. Thus, it is possible that an insect egt gene might be a suitable target for novel insect control strategies. The disclosure of the present invention provides the means for designing such strategies. For instance, as a fifth preferred embodiment of the present invention, ecdysteroid analogs which bind to the EGT enzyme, but which cannot be cleaved and released from the enzyme can be designed. Such "suicide substrates" will competitively bind to and inhibit or block the action of the EGT enzyme and consequently interfere with the development of the insect pest. Alternatively, recombinant organisms can be genetically engineered so that expression of the insect egt gene is prevented through the production of anti-sense RNA, for example.

It will be understood by those skilled in the art that the insect pests can be exposed to the insect control agent of the present invention by conventional methods such as allowing the insect to ingest, inhale or directly contact an organism containing the insect control agent.

Finally, it is apparent that the disclosures of this invention will be of considerable import and utility to the study of insect physiology and development. The egt gene, gene product, antibodies directed against the latter, and all other reagents derived from or connected with the above will be valuable tools for the investigation and manipulation of the regulatory mechanisms which control the processes of insect development.

This invention is further illustrated by the following examples, which are not to be construed in any way as imposing limitations on the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE I

The position of the egt gene on the AcMNPV genome is illustrated in FIG. 1. A scale in map units is presented above the map of the AcMNPV genome in FIG. 1. To determine the nucleotide sequence of this gene and flanking regions, and to allow for subsequent manipulation of the gene, it is first necessary to clone several DNA fragments encompassing this region into plasmid vectors (see T. Maniatis, E. F. Fritsch, and J. Sambrook, "Molecular Cloning: A Laboratory Manual." Cold Spring Harbor Laboratory; Cold Spring Harbor, N.Y., 1982, for standard cloning procedures). Panel A shows a linear map of the AcMNPV genome after cleavage with restriction endonucleases EcoRI and HindIII. Panel B is an enlargement of the genome from 7.6 to 11.1 map units showing the location of the egt gene. The original AcMNPV strain used is the L1strain (H. H. Lee and L. K. Miller, *J. Virol.*, 27:754, 1978). The different DNA fragments which are cloned, and the names of the resultant plasmids, are illustrated in Panel C of FIG. 1. Fragment 1, which extends from a PstI site at 7.6 mu to a BamHI site at 11.1 mu, is cloned into the plasmid vector pUC19, while fragments 2 and 3 [from PstI (7.6 mu) to EcoRI (8.65 mu), and from EcoRI (8.65 mu) to SalI (10.5 mu) respectively] are both cloned into the vectors Bluescript M13$^+$ and Bluescript M13$^-$ (Stratagene, La Jolla, Calif.). Fragment 4 [BstEII (8.35 mu) to BstEII (8.7 mu)] is cloned into Bluescript M13$^+$.

A large number of subclones of BCPsE and BCES plasmids are then generated (S. Henikoff, *Gene*, 28:351, 1984). These subclones have progressively larger deletions of the viral insert so that they contain differing amounts of viral DNA, ranging from less than 50 base pairs to the entire viral fragment. Many of these subclones, as well as the plasmid BCB, are then sequenced, (F. Sanger, S. Nicklen, and A. Coulson, *Proc. Nat'l. Acad. Sci. USA*, 74:5463, 1977), so that the entire egt gene has been sequenced in both directions. The extent of sequence determined from each subclone is indicated in FIG. 2, Panel A. The nucleotide sequence obtained is then analyzed by computer for the presence of open reading frames which can encode proteins. The results of this analysis, which are presented in FIG. 2, Panel C, indicate that the egt gene can encode a protein of 506 amino acids. The nucleotide sequence of the egt gene, and the predicted amino acid sequence of the egt gene product, are presented in FIG. 3.

EXAMPLE II

To construct recombinant viruses incapable of expressing a functional egt, gene, further manipulation of the plasmid clones described in Example I is first required. The plasmid pUCPsB is cleaved with the restriction endonucleases EcoRI and XbaI (see FIG. 4 for the positions at which these enzymes cut within the egt gene) and the intervening fragment discarded. The *Escherichia coli* lacZ gene, which encodes the enzyme β-galactosidase, is then inserted between the EcoRI and XbaI sites. The resultant plasmid is designated pEGTZ.

In this plasmid, the position of the lacZ gene is such that it is in frame with the preceding egt coding sequences. Alternatively, the plasmid pEGTDEL is constructed by simply ligating the EcoRI and XbaI sites together (after both sites have been blunt-ended) without inserting any sequences between them.

The plasmid pEGTZ is then cotransfected with wt AcMNPV DNA into *Spodoptera frugiperda* (fall armyworm) IPLB SF21 (SF) cells (insect cells used as hosts for AcMNPV). This procedure allows for recombination to take place between homologous sequences in the viral and plasmid DNAs. Recombination at either side of the egt gene results in the replacement of the viral egt gene with the egt-lacZ gene fusion from the plasmid. Because the remaining egt coding sequences are in frame with the lacZ sequences, such a recombinant virus will produce a fusion protein comprising the first 84 amino acids of EGT, joined to β-galactosidase. The desired virus, termed vEGTZ, can then be identified by virtue of the fact that β-galactosidase expression will give rise to blue viral plaques in the presence of a chromogenic indicator such as X-gal. A diagram of the egt gene of vEGTZ is presented in FIG. 4.

The recombinant virus vEGTDEL is then obtained by cotransfecting the plasmid pEGTDEL and DNA from the virus vEGTZ into SF cells. Homologous recombination similar to that described above results in the replacement of the egt-lacZ fusion gene in vEGTZ with the deleted egt gene from pEGTDEL. The recombinant virus vEGTDEL is then identified due to the fact that it can no longer form blue plaques in the presence of X-gal. The structure of the egt gene of vEGTDEL is shown in FIG. 4.

EXAMPLE III

The product of the egt gene is identified by comparing proteins synthesized by wt AcMNPV (which makes EGT) to those produced by vEGTZ or vEGTDEL (which cannot make EGT). SF cells are infected either with wt AcMNPV or with vEGTZ at a multiplicity of infection (MOI) of 20. Cells which are not infected with either virus are also analyzed. After 6 hours of infection, the cells are incubated in the presence of the radioactively labeled amino acid [$^{35}$S]-methionine for 1 hour. This procedure results in the radioactive labeling of all proteins which are made in the cell during the 1 hour period. The cells are then lysed and the proteins separated by SDS-polyacrylamide gel electrophoresis (SDS-PAGE). Any proteins which had been secreted from the cells are also harvested and analyzed. After SDS-PAGE, the radiolabeled proteins are detected by exposing the gel to X-ray film. FIG. 5 shows that a 60,000 Da protein is secreted from wt AcMNPV-infected cells (lane 5) but not from vEGTZ-infected cells (lane 6) or uninfected cells (lane 4). This 60,000 Da protein can not be detected in lysates of wt-AcMNPV infected cells (lane 2) showing that it is primarily secreted from the cell. These data demonstrate that the product of the egt gene is a 60,000 Da protein which is secreted from the cell, properties which are in good agreement with the nucleotide and amino acid sequence data.

EXAMPLE IV

The enzymatic activity of the EGT protein is also identified by comparing wt AcMNPV and vEGTZ. SF cells are infected with wt AcMNPV or vEGTZ as described in Example III. Twelve hours pi the cells and extracellular media are collected and processed separately. Uninfected cells are treated in parallel. Cell lysates or extracellular media are incubated in the presence of 10 mM UDP-glucose and 0.25 μCi [$^3$H]ecdysone. The presence of ecdysteroid UDP-glucosyl transferase activity in the cell lysates or media will catalyse the transfer of glucose from the UDP-glucose to the ecdysone, forming an ecdysone-glucose conjugate. Ecdysone and the ecdysone-glucose conjugate are separated from one another by silica gel thin layer chromatography (S. K. Bansal and T. Gessner, *Anal. Biochem.*, 109:321, 1980). They are visualized by exposing the chromatogram to X-ray film. FIG. 7, Panel A shows that ecdysone-glucose conjugates (G) are only formed when wt AcMNPV-infected cell lysates or extracellular medium are assayed. No conjugates are observed when uninfected or vEGTZ-infected cells or media are used, showing that the activity is due to the expression of egt. Most of the activity is observed in the extracellular medium (compare lanes C and M) in agreement with the data discussed above in Example III. Proof that glucose is in fact being conjugated to ecdysone is obtained by assaying wt-infected lysates as described above except that the UDP-glucose is replaced with the radiolabeled UDP-[U-$^{14}$C]glucose. Panel B of FIG. 7 shows the comparison of reactions carried out with unlabeled UDP-glucose and labeled UDP-[U-$^{14}$C]glucose (compare lanes 1 and 2). [$^3$H]ecdysone is still present in both reactions. Scintillation counting of the conjugate in lane 2 shows that both $^3$H (from the ecdysone) and $^{14}$C (from the glucose) can be detected. These data demonstrate that the egt gene product is a UDP-glucosyl transferase which catalyses the transfer of glucose from UDP-glucose to ecdysone.

Experiments are then performed to investigate more thoroughly the substrate specificity of EGT. In these experiments (see Table 1 below) various substrates (concentration 1 mM) are incubated in the presence of extracellular medium from wt-AcMNPV infected cells, which is shown above to contain significant EGT activity. As controls to ensure that any conjugation observed is due to EGT, each substrate is also incubated with media from uninfected and vEGTZ-infected cells, which cannot produce EGT: 0.05 μCi UDP-[U-$^{14}$C]glucose are added to each reaction. Any compounds which can function as substrates for EGT will be conjugated with glucose; they can be identified by virtue of the fact that the glucose is radioactively labeled. One further control is the addition of UDP-[U-$^{14}$C]glucuronic acid to a separate set of reactions with medium from wt-infected cells. This was to demonstrate that glucuronic acid is not transferred by this reaction. The data obtained are presented in Table 1 below. It can be seen that the only substrates identified are ecdysone, 20-hydroxyecdysone and makisterone A. These are all ecdysteroids. No conjugation is ever observed using medium from mock or vEGTZ-infected cells confirming that the activity observed is due to expression of egt. No conjugation is observed when UDP-[U-$^{14}$C]glucuronic acid is used, demonstrating that EGT does not transfer glucuronic acid.

TABLE 1

Substrate specificity of EGT gene product

| Substrate | Mock (pmol Glucose transferred) | wild type (pmol Glucose transferred) | vEGTZ (pmol Glucose transferred) | wild type (pmol Glucuronic acid transferred) |
|---|---|---|---|---|
| p-Aminobenzoic acid | — | — | — | — |
| Bilirubin | — | — | — | — |
| Chloramphenicol | — | — | — | — |
| Diethylstilbestrol | — | — | — | — |
| Ecdysone | — | 155.7 | — | — |
| β-Estradiol | — | — | — | — |
| Hydroxyecdysone | — | 87.8 | — | — |
| Hydroxyquinoline | — | — | — | — |
| Makisterone A | — | 89.6 | — | — |
| -Menthol | — | — | — | — |
| Methylumbelliferol | — | — | — | — |
| α-Napthol | — | — | — | — |
| p-Nitrophenol | — | — | — | — |
| Phenolphthalein | — | — | — | — |
| Testosterone | — | — | — | — |
| α-Tetralol | — | — | — | — |

Substrates are incubated in the presence of medium derived from appropriately infected cells and 0.05 μCi UDP-[U-$^{14}$C]glucose or UDP-[U-$^{14}$C]glucuronic acid. Amounts of glucose or glucuronic acid transferred are calculated after scintillation counting of the appropriate regions of the chromatography plates.

EXAMPLE V

Figure 9:
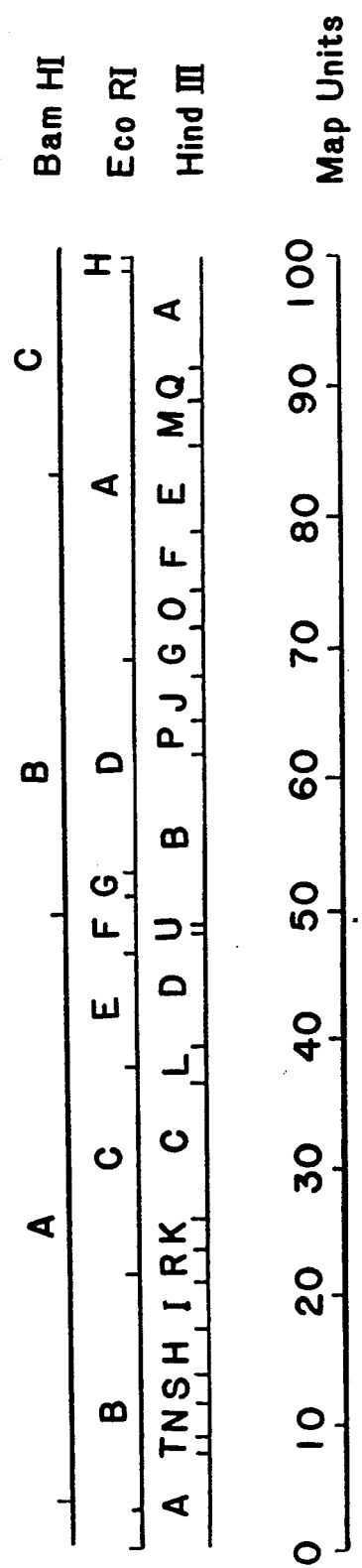
FIG. 9 is a schematic representation of the OpMNPV genome.

To demonstrate that other baculoviruses also contain an egt gene, the DNA of the baculovirus OpMNPV is isolated and digested separately with the restriction endonucleases EcoRI, BamHI, and HinDIII. These enzymes cleave the viral DNA into several fragments of different sizes whose positions on the OpMNPV genome are already known (D. Leisy, G. F. Rohrmann and G. S. Beaudreau, J. Virol., 52:699, 1984). The different sized fragments are separated by agarose gel electrophoresis and then transferred to a nylon membrane by a procedure known as Southern blotting (T. Maniatis, E. F. Fritsch, and J. Sambrook, "Molecular Cloning: A Laboratory Manual," Cold Spring Harbor laboratory; Cold Spring Harbor, N.Y., 1982). A fragment of the AcMNPV egt gene is excised from the plasmid BCES with the enzymes EcoRI and XbaI (as shown in FIG. 4). This fragment is radioactively labeled with $^{32}$P and then used as a probe to identify any related sequences in the OpMNPV genome. Under appropriate conditions, a DNA fragment such as this will bind to another fragment of DNA which contains sequences similar or identical to it. Thus, the AcMNPV egt probe should bind to any OpMNPV DNA fragments on the nylon membrane which contain related DNA sequences. The position of the bound probe can be visualized by exposing the membrane to X-ray film. FIG. 8 shows that the AcMNPV egt probe binds to specific fragments of OpMNPV DNA, namely, EcoRI fragment B, BamHI fragment A and HindIII fragments N and S. Note that the OpMNPV egt gene is at the same relative position in the genome as the AcMNPV gene (FIG. 9).

EXAMPLE VI

Hemolymph titers of ecdysteroids fluctuate in a cyclic manner to regulate both larval-larval and larval-pupal molts (Reviewed in: "Comprehensive Insect Physiology, Biochemistry And Pharmacology," G. A. Kerkut and L. I. Gilbert, Eds., Vols. 7 and 8, Pergamon Press, Oxford, 1984). Since glucose conjugation is suspected to inactivate ecdysteroids (J. T. Warren, B. Steiner, A. Dorn, M. Pak, L. I. Gilbert, J. Liq. Chromatography 9:1759, 1986; M. J. Thompson et al., Arch. Insect Biochem. Physiol., 4:1, 1987; M. J. Thompson, J. A. Svoboda, R. Lozano, and K. R. Wilzer, Arch. Insect Biochem. Physiol., 7:157, 1988), it is probable that egt expression during AcMNPV infection disrupts the normal developmental process of the infected insect. To demonstrate such a disruption, newly-ecdysed fourth instar S. frugiperda larvae are infected by injection with wt AcMNPV or vEGTZ and monitored daily for any perturbations in their development. One cohort of larvae is injected with tissue culture fluid as a negative control. The results of this experiment are presented in Table 2 below. All larvae injected with tissue culture fluid (mock-infected) molt to fifth instar as expected. Only one of sixteen larvae infected with wt virus make this transition. In contrast, all larvae infected with the mutant vEGTZ undergo a fourth-to-fifth instar molt. Thus, it is clear that egt expression by wt AcMNPV specifically inhibits host molting. Both infected groups of larvae subsequently succumb to the viral infection, showing that disruption of egt does not prevent vEGTZ from completing its infectious cycle.

Similar results are obtained with larvae injected at early fifth instar. Using newly ecdysed fifth instar larvae, no wt-infected larvae show any signs of pupation, which the majority of vEGTZ-infected insects display several behavioral modifications (feeding cessation, wandering, and spinning) characteristic of an impending larval-pupal molt. However, all virus-infected animals died before pupation. These data show that AcMNPV infection prevents the insect larvae from molting or pupating. Further, the data show that this disruption of the insects' development is due to the expression of egt.

TABLE 2

| Virus | Molting | Mortality |
|---|---|---|
| Mock | 16 | 0 |
| Wild Type | 1 | 16 |
| vEGTZ | 16 | 16 |

Inhibition of molting by AcMNPV infection. Fourth instar S. frugiperda larvae are injected with 1 × 10$^5$ pfu wt AcMNPV or vEGTZ in 5 μl. Mock-infected larvae are injected with 5 μl tissue culture fluid. Each cohort includes 16 larvae which are maintained on artificial diet, (R. L. Burton, ARS publication, pp. 33–134, 1969) at 28° C. with a 14:10 hour light:dark cycle. Larvae are monitored daily for ecdysis, and mortality is recorded at day 7.

EXAMPLE VII

In vivo bioassays of both wild-type (wt) AcMNPV and vEGTZ reveal that the egt gene allows the virus to prolong the length of time the infected larvae spend feeding and that deletion of egt improves the characteristics of the virus as a pesticide. In these studies, *S. frugiperda* larvae are injected either with wt AcMNPV or vEGTZ early in the 4th instar. For comparison, some larvae are injected with tissue culture medium containing no virus. The larvae are then checked daily for weight gain, signs of molting or pupation, and mortality. The average daily weight gains of the different group of larvae, along with the percent mortality, are plotted in FIGS. 10 and 11 respectively. The control insects show moderate growth for the first two days. During the second day, they all molt to 5th instar. They then grow dramatically for two more days before they stop feeding in preparation for pupation. Only 1 out of 16 wt AcMNPV-infected larvae molt, and instead they show continuous growth for three days following infection. At this stage, they begin to get sick, but no larvae die until day 5. All wt AcMNPV-infected larvae are dead by day 6. In contrast, all vEGTZ-infected larvae undergo a 4th to 5th instar molt and during this period, they cease to feed. This accounts for the absence of growth from day 1 to day 2. After molting, they resume feeding but also began to show signs of sickness by day 3. They begin to die 4 days after infection and are all dead by day 5. Thus, when the infected larvae are allowed to carry out their normal development during infection (with vEGTZ), they display reduced feeding and die sooner after infection.

Figure 12:
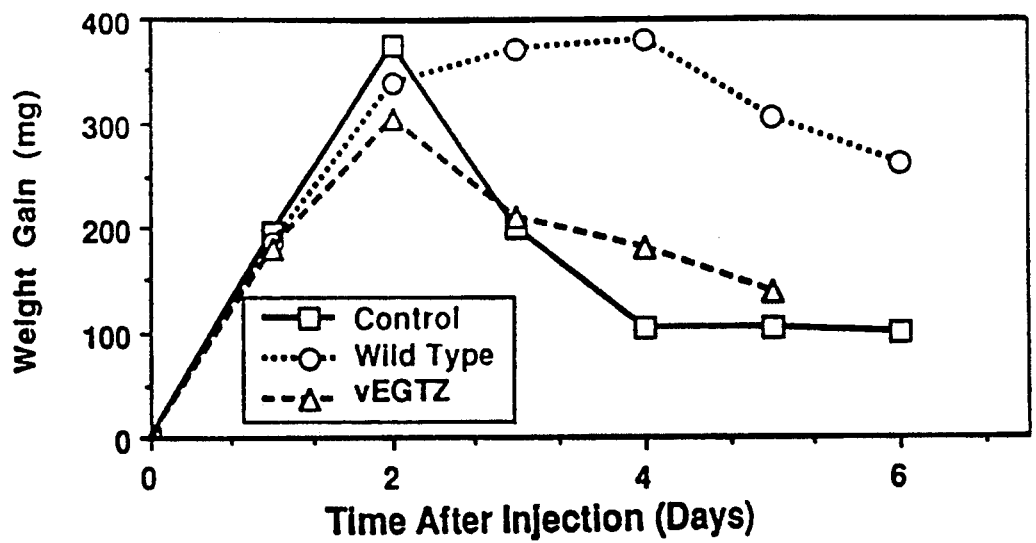
FIG. 12 is a graph of the weight gain after infection of larvae at 5th instar with wt AcMNPV or vEGTZ.
Figure 13:
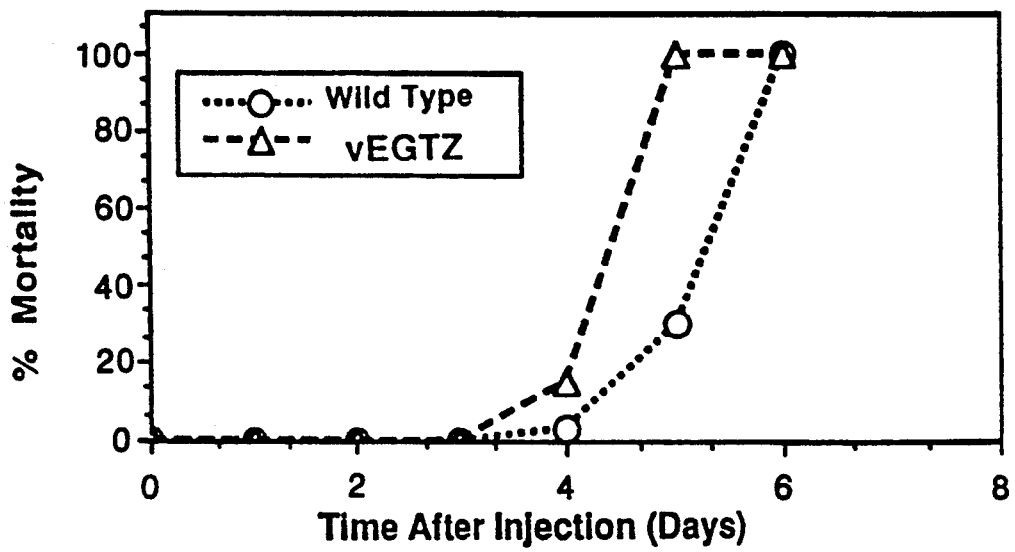
FIG. 13 is a graph of larval mortality after infection of larvae at 5th instar with wt AcMNPV or vEGTZ.

These phenomena are even more clearly observed following infection of 5th instar larvae (FIGS. 12 and 13). As expected, control larvae show considerable growth for two days before they stop feeding in preparation for pupation. This feeding cessation is accompanied by a dramatic weight loss. Wt AcMNPV-infected larvae show no signs of such a feeding cessation; they continue to feed and gain weight for another two days before they begin to get sick. These larvae do not all die until seven days after infection. In sharp contrast, it can be seen that vEGTZ-infected larvae, like the controls, only feed for the first two days after infection. After this point, there is a dramatic weight loss as they prepare for pupation. However, none of these larvae actually pupate; they show signs of illness by day three and are all dead six days after infection. Again, vEGTZ infection brings about reduced feeding and earlier death.

EXAMPLE VIII

Example VII involves injection of the recombinant virus into late instar *S. frugiperda* larvae, and shows that vEGTZ infection leads to reduced feeding and earlier death compared to infection by wild-type (wt) AcMNPV. In this example, the effects of vEGTZ and wt AcMNPV infection on newly-hatched first instar *S. frugiperda* larvae are compared. In the experiment presented in FIGS. 14 and 15, neonate *S. frugiperda* are fed on a diet containing various concentrations of vEGTZ or wt AcMNPV polyhedral inclusion bodies (PIBs) (this is the normal mechanism for infection of insects in the wild), and monitored daily for mortality. The results obtained for two separate doses are presented in the FIGS. 14 and 15 at virus concentrations of $4.8 \times 10_6$ PIBs/ml and $2.4 \times 10^6$ PIBs/ml, respectively. It can be seen that, at both doses, vEGTZ-infected larvae show considerable mortality substantially sooner than larvae infected with the wt virus. In general, larvae infected with the recombinant virus are killed between three and four days earlier than wt-infected larvae. This result is further evidence that baculoviruses altered in the same way as vEGTZ would function better as biological pesticides.

It should be understood, of course, that the foregoing relates only to preferred embodiments of the present invention and that numerous modifications or alterations may be made therein without departing from the spirit and the scope of the invention as set forth in the appended claims.

We claim:

1. An insect control agent, wherein said insect control agent is a nuclear polyhedrosis virus in which a naturally occurring gene encoding an ecdysteroid UDP-glucosyl transferase is inactivated.

2. The insect control agent of claim 1 wherein said nuclear polyhedrous virus is selected from the group consisting of *Autographa californica* nuclear polyhedrosis virus and *Orgyia pseudotsugate* nuclear polyhedrosis virus.

3. The insect control agent of claim 2 wherein said insect control agent is one of vEGTZ and vEGTDEL.

4. A method for producing an improved insect control agent, comprising the step of inactivating a gene encoding an ecdysteroid UDP-glucosyl transferase in a nuclear polyhedrosis virus, said gene being a naturally occuring part of the genome of said nuclear polyhedrosis virus.

5. The method of claim 4 wherein the nuclear polyhedrosis virus is selected from the group consisting of *Autographa californica* nuclear polyhedrosis virus and *Orgyia pseudotsugata* nuclear polyhedrosis virus.

* * * * *

UNITED STATES PATENT AND TRADEMARK OFFICE
CERTIFICATE OF CORRECTION

PATENT NO. : 5,180,581

DATED : Jan. 19, 1993

INVENTOR(S) : Lois K. Miller; David R. O'Reilly

It is certified that error appears in the above-identified patent and that said Letters Patent is hereby corrected as shown below:

On the cover page, column 2, last cited reference, please rewrite "Kunmar," as --Kumar,--. At column 3, line 10, please insert --amount of feeding by the insect before the insect succumbs to-- after "the", first occurrence. At column 3, lines 37, 38 and 40, each occurrence, please rewrite "(EGT)" as --EGT--. At column 6, line 50, please insert --and-- between "M13+" and "Bluescript". At column 13, seventh entry of Table, please rewrite "Hydroxyecdysone" as --20-Hydroxyecdysone--. At column 16, line 36, please rewrite "*pseudotsugate*" as --*pseudotsugata*--.

Signed and Sealed this

First Day of March, 1994

Attest:

BRUCE LEHMAN

Attesting Officer

Commissioner of Patents and Trademarks